US00PP25222P3

(12) United States Plant Patent
Delbard

(10) Patent No.: US PP25,222 P3
(45) Date of Patent: Jan. 13, 2015

(54) APPLE TREE NAMED 'DELCORED'

(50) Latin Name: ***Malus pumila* Mill.**
Varietal Denomination: Delcored

(71) Applicant: Societé Nouvelle Pépinières et Roseraies Georges Delbard SAS, Malicorne (FR)

(72) Inventor: Arnaud Delbard, Malicorne (FR)

(73) Assignee: Societé Nouvelle Pépinières et Roseraies Georges Delbard SAS, Malicorne (FR)

( * ) Notice: Subject to any disclaimer, the term of this patent is extended or adjusted under 35 U.S.C. 154(b) by 64 days.

(21) Appl. No.: 13/815,714

(22) Filed: Mar. 15, 2013

(65) Prior Publication Data

US 2014/0283237 P1 Sep. 18, 2014

(51) Int. Cl.
*A01H 5/00* (2006.01)

(52) U.S. Cl.
USPC ..... Plt./161

(58) Field of Classification Search
USPC ..... Plt./161
See application file for complete search history.

*Primary Examiner* — Kent L Bell
(74) *Attorney, Agent, or Firm* — Buchanan, Ingersoll & Rooney PC

(57) ABSTRACT

The new apple tree cultivar was formed by the crossing of the 'Delblush' and 'CO-OP 30' cultivars. Attractive large bright red-purple fruit is formed wherein such coloration is influenced by the degree of exposure to sunlight. The tree displays a medium-to-large semi-upright to spreading growth habit. The fruit harvest time is late in the season. The fruit flesh is very firm and displays a pleasant juicy sweet taste upon maturity. A quality dessert apple fruit crop is provided.

4 Drawing Sheets

Botanical/commercial classification: *Malus pumila* Mill./ Apple Tree.

Varietal denomination: cv. Delcored.

SUMMARY OF THE INVENTION

The new apple tree cultivar was created by artificial pollination during 1994 at Malicorne, France wherein two parents were crossed in the hope that they would contribute to the desired characteristics. The female parent (i.e., seed parent) was the 'Delblush' cultivar (U.S. Plant Pat. No. 10,276). The male parent (i.e., pollen parent) was the 'CO-OP 30' cultivar (U.S. Plant Pat. No. 9,193). The parentage of the new cultivar of the present invention can be summarized as follows:

'Delblush'×'CO-OP 30'.

Seeds resulting from the pollination were sown and 13 small plantlets were obtained which were physically and biologically different from each other. Selective study culminating in 2003 resulted in the identification of a single plant of the new cultivar of the present invention.

The new cultivar was found to exhibit the following combination of characteristics:

(a) displays a medium-to-large semi-upright to spreading growth habit,
(b) forms attractive large fruit that commonly is ready for harvest later in the season,
(c) forms in good yield generally large bright red-purple fruit having an excellent keeping quality wherein the skin coloration is influenced by the degree of exposure to sunlight, and
(d) displays very firm fruit flesh having a pleasant juicy sweet flavor upon maturity.

The new cultivar can be readily distinguished from its ancestors and all other apple cultivars known to the originator.

More specifically, the 'Delblush' cultivar forms yellow fruit having an orange overcolor on a portion of the skin, and the 'CO-OP 30' cultivar forms Saffron-Yellow fruit having a Cardinal Red overcolor fading to orange.

When compared to the 'Golden Delicious' variety (non-patented in the United States, the new variety displays more vigor and stronger branches, commonly flowers a few days earlier, and yields fruit that is ready for harvest approximately two weeks later.

The new apple cultivar has been found to readily undergo asexual propagation and can be reproduced by conventional routes, such as budding (i.e., eye grafting). This asexual reproduction as performed at Malicorne, France has demonstrated that the characteristics of the new cultivar are strictly transmissible from one generation to another and are firmly fixed. Representative rootstocks that can be used with the new cultivar include PAJAM® brand of 2 Cepiland, M9EMLA and M9NAKB. Other rootstocks also can be considered and utilized taking into consideration the soil and other environmental conditions that are to be encountered at a particular growing site.

The new cultivar of the present invention has been named 'Delcored'.

BRIEF DESCRIPTION OF THE PHOTOGRAPHS

The accompanying photographs show typical specimens of the new cultivar as depicted in color as nearly true as it is reasonably possible to make the same in color illustrations of this character. The plant material shown in the photographs was budded on PAJAM® brand of 2 Ceipland rootstock and was being grown at Malicorne, France during October.

DETAILED DESCRIPTION

Figure 1:
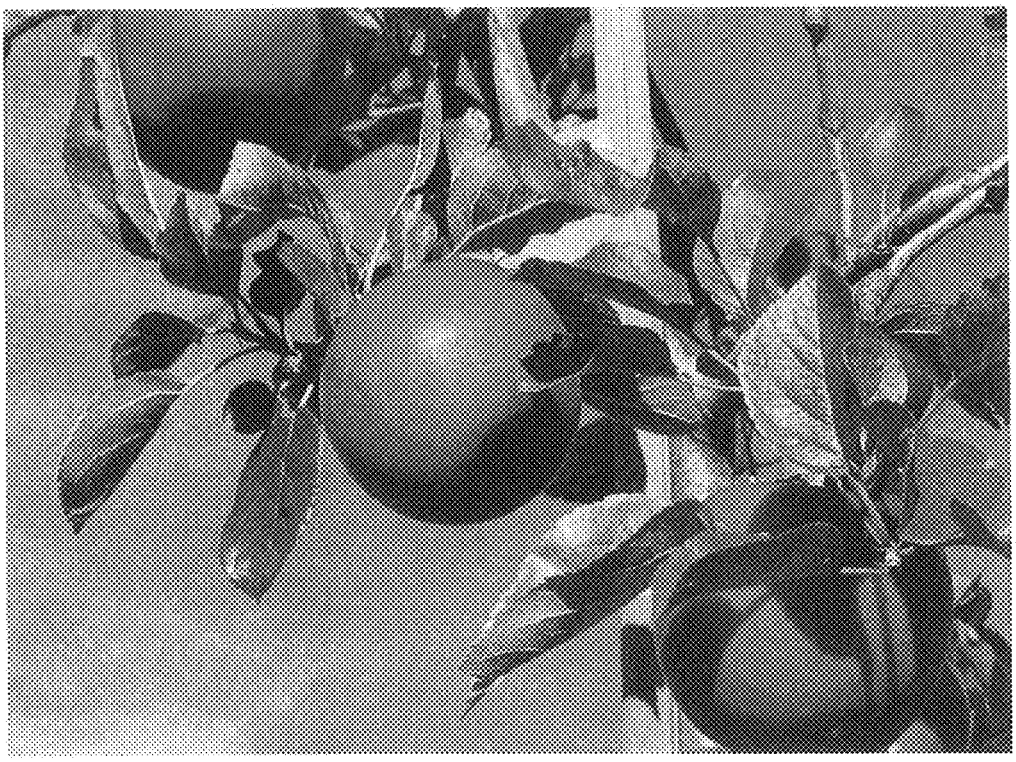
FIG. 1 illustrates specimens of typical foliage and bright purple-red mature fruit ready for harvest.
Figure 2:
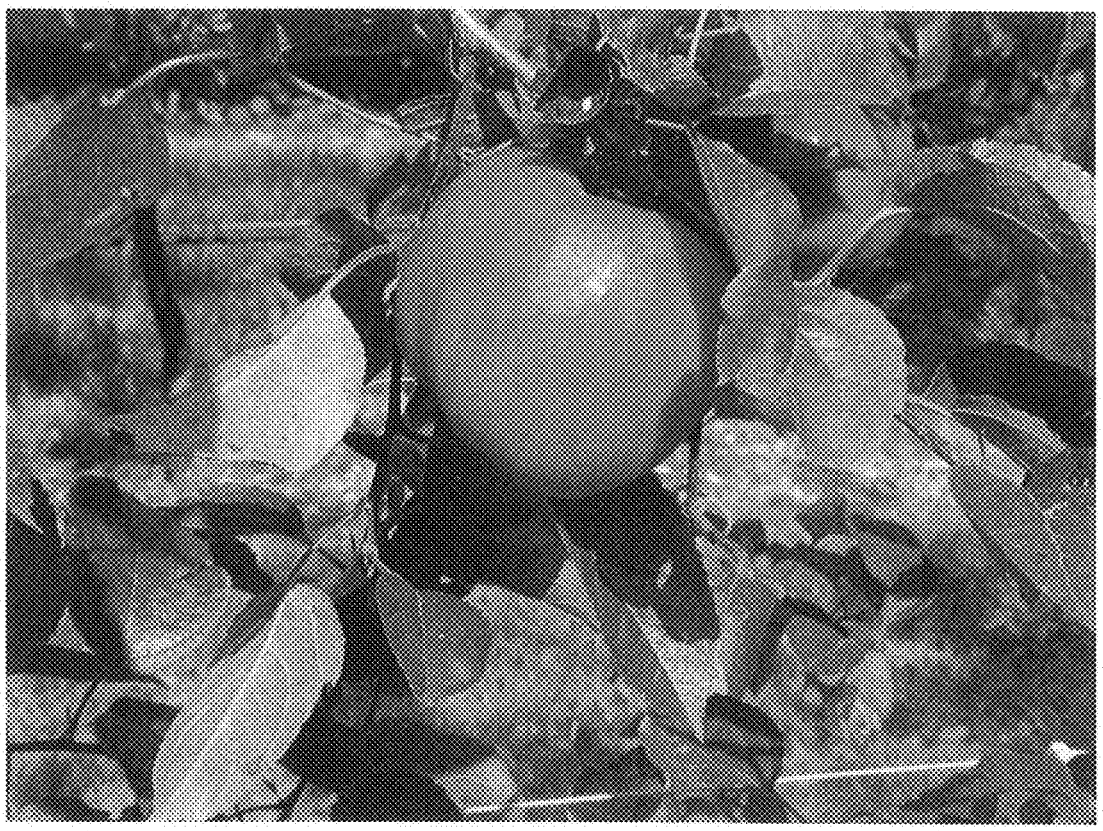
FIG. 2 illustrates a closer view of a specimen of a typical bright red-purple fruit when exposed to the sun ready for harvest as well as the upper and under surfaces of the foliage.
Figure 3:
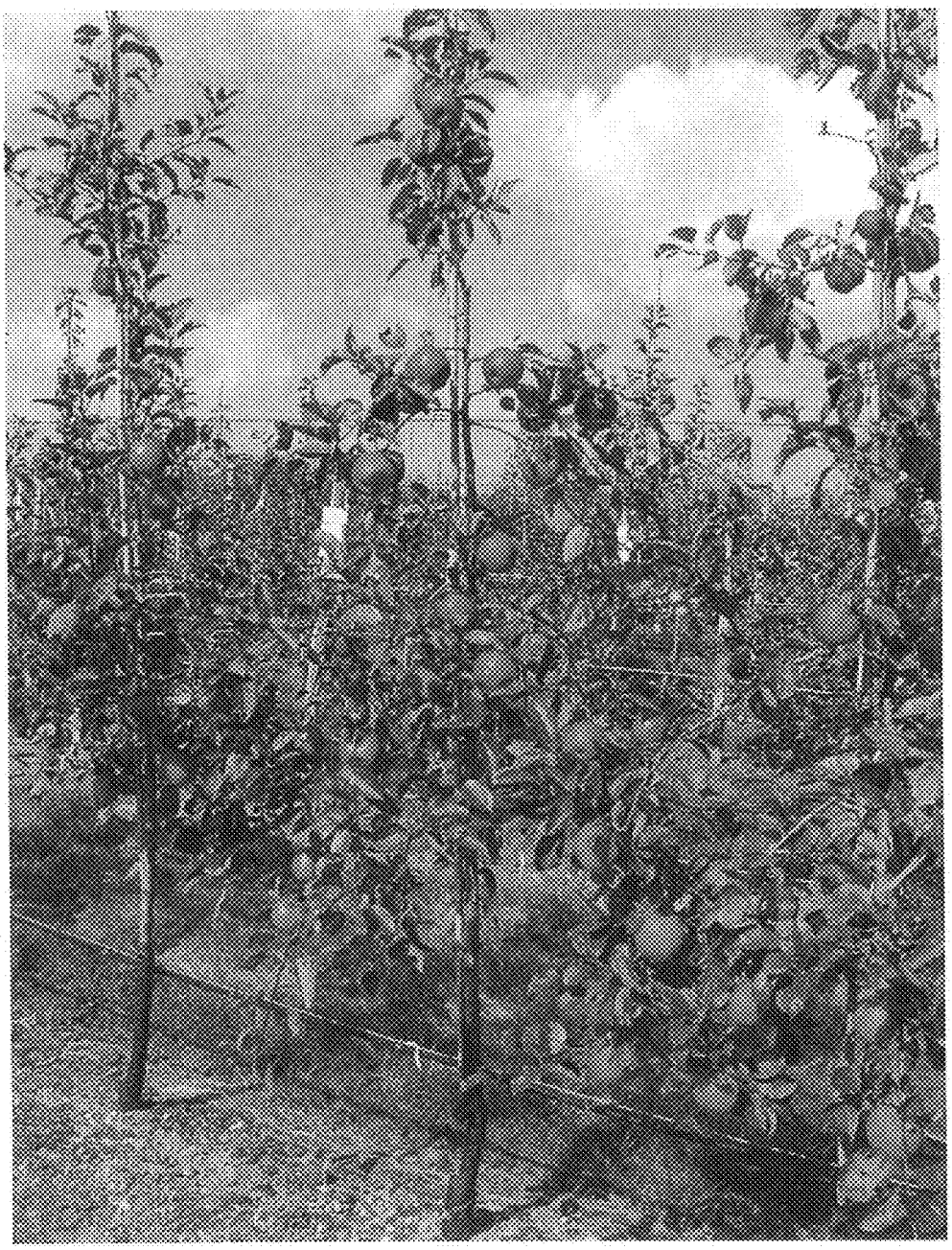
FIG. 3 illustrates specimens of typical fruit-bearing young trees in an orchard setting.
Figure 4:
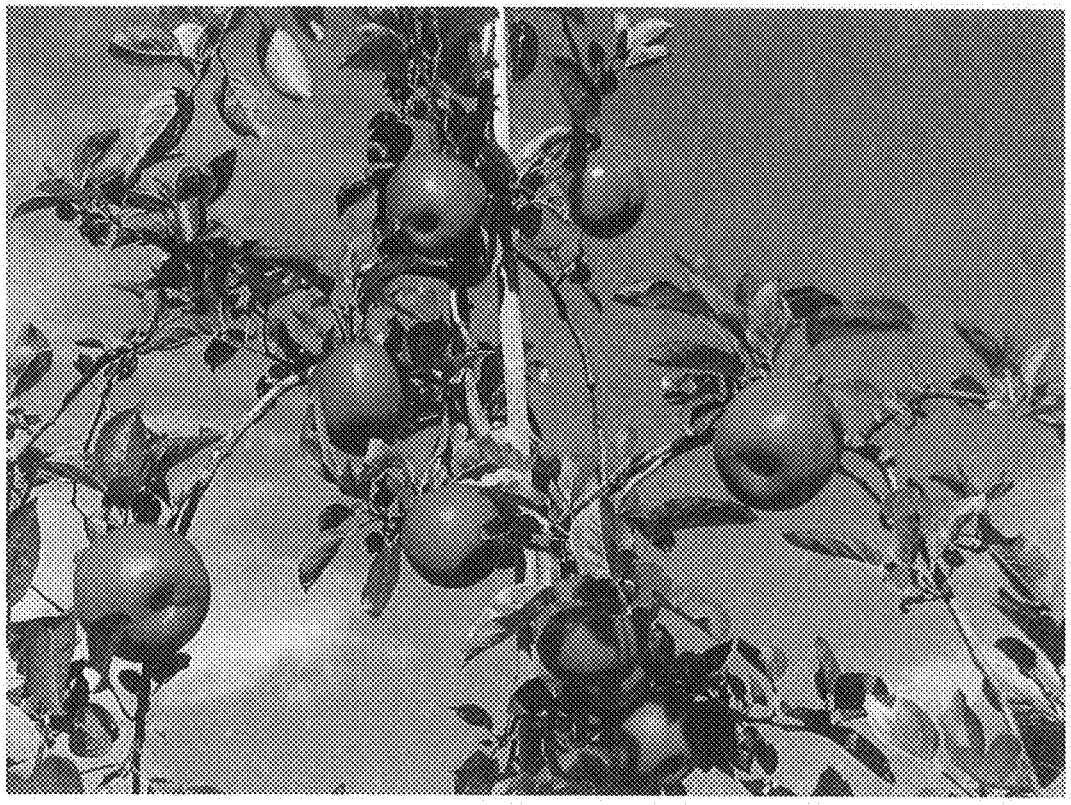
FIG. 4 illustrates specimens of fruit ready to harvest wherein a typical fruit disposition is displayed.

The following is a detailed description of the new cultivar of the present invention. The description is based upon the observation of approximately eight-year-old trees (except as otherwise indicated) when grown at Malicorne, France, during the 2011-2012 growing season. The plants had been asexually reproduced while grafted on PAJAM® brand of 2 Cepiland rootstock (non-patented in the United States). The chart used in the identification of colors is that of The Royal Horticultural Society, London, England (R.H.S. Colour Chart—2001 Edition). When coloration in common terms is provided, such coloration is to be accorded its ordinary dictionary significance.

Classification: *Malus Pumila*, Mill.

Tree:

*Size*.—Medium-to-large, at eight years of age commonly approximately 2.5 meters in height and approximately 1.8 meters in width.

*Growth habit*.—Semi-upright and spreading, ramified, and somewhat drooping.

*Vigor*.—Medium vigor to vigorous when grown on standard 'M9' rootstock.

*Fruit bearing*.—Appears on one-year-old shoots.

*Trunk diameter*.—Approximately 5 to 6 cm measured one meter above the soil for a tree of 7 years.

*Trunk color*.—Greyed-Green Group 197B.

*Branch texture*.—Generally smooth.

*Branch color*.—Grey-green commonly with some Greyed- Purple Group 187A for one-year-old shoots when fruit is at commercial maturity.

*Branch habit*.—Generally considered to be moderate-to-strong for the species.

*Branch lenticels*.—Commonly approximately 2 mm in length, approximately 1 mm in width, and near Greyed-Yellow group 161A in coloration.

*Crotch angle*.—Typically near 65 degrees measured in the horizontal plane.

*Annual growth*.—Commonly approximately 11 to 25 cm when measured on extension shoots arising from branches approximately 1.5 meters above ground level.

*Internodes*.—On one-year-old shoots commonly approximately 16 to 23 mm in length and approximately 6 to 7 mm in thickness measured at the center of the middle internode.

*Pubescence*.—Slight.

*Bark lenticels*.—Commonly approximately 5 or 6 per square centimeter, approximately 4 mm in length, approximately 1 mm in width, and near Greyed-Orange Group 164B in coloration.

Foilage:

*Leaves*.—Overall shape — elliptic. Length — commonly approximately 9.5 to 12.5 cm on average without petiole. Width — commonly approximately 7 to 9.5 cm on average. Apex — acute. Base — obtuse. Margin — serrated. Texture — smooth on the upper surface, and with some roughness on the under surface. Color — near Green Group 137A on the upper surface, and near Green Group 139C on the under surface. Venation — reticulate, near Green Group 140A on the upper surface, and near Yellow-Green Group 149A on the under surface.

*Petioles*.—Length — commonly approximately 4 cm on average. Diameter — commonly approximately 3 mm on average. Color — commonly near Green Group 143A on the upper surface, and near Red Group 53A on the under surface.

*Pedicels*.—Length — commonly approximately 2.5 to 3 cm on average. Diameter — commonly 2 to 4 mm on average. Color — commonly bicolored, Greyed-Orange Group 166A and Yellow-Green Group 152B.

*Stipules*.—Number — commonly 2 per leaf. Length — commonly approximately 1.1 cm on average. Width — commonly approximately 1 to 2 mm on average. Color — commonly near Green Group 139C.

Flowers:

*Time*.—Commonly commence at mid-April at Malicorne, France.

*Bud color*.—Red-Purple Group 59D.

*Bud shape*.—Cupuliforme.

*Bud length*.—Approximately 10 mm.

*Bud width*.—Approximately 8 mm at the widest point.

Fruit:

*Maturity*.—Late harvest date, commonly approximately September 25$^{th}$ to October 10$^{th}$ at Malicorne, France, and approximately 2 weeks later than the 'Golden Delicious' cultivar (non-patented in the United States) at such location.

*Size*.—Large.

*Width*.—Commonly approximately 8.4 cm on average.

*Height*.—Commonly approximately 7.4 cm on average.

*Weight*.—Commonly approximately 220 grams on average with fruit size and weight being influenced by the cultural practice being employed.

*Shape*.—Generally cylindrical.

*Stem cavity*.—Approximately 25 to 30 mm in width on average, and 19.3 mm in depth on average, and commonly with shades of Yellow-Green Group 153B.

*Eye*.—Small, commonly with a partially open aperture, and with a basin approximately 13.8 mm in width on average and approximately 15 mm in depth on average.

*Stem*.—Commonly approximately 16 to 23 mm in length on average and commonly approximately 2.5 to 3.5 mm in thickness on average.

*Skin texture*.—Relatively thick, smooth and shiny.

*Bloom*.—Present on fruit skin.

*Cracking*.—Absent with commonly no tendency for the fruit skin to crack.

*Background*.—The fruit background color commonly is Yellow-Orange Group 14B when mature.

*Overcolor*.—Commonly approximately 90% of the fruit skin surface bears a coloration of near Red-Purple Group 60B when mature. The extent of the overcolor on the mature fruit is influenced by the location of the fruit on the tree and the corresponding level of sunlight encountered during the ripening.

*Russeting*.—Commonly absent or sparsely present at the stem and eye cavities.

*Lenticels*.—Generally round in shape, small, and commonly approximately 0.5 mm in diameter.

*Firmness*.—Crunchy, very firm fruit flesh and commonly approximately 8 to 9 Kg per square cm at harvest.

*Flavor/aroma*.—Fruity, refreshing, pleasant to the mouth, very juicy and crisp sweet flavor, good balance of sugar/acidity with a Brix commonly near 14 on average, and a good overall eating quality.

*Flesh color*.—Near White Group 155A, with slow browning when exposed to air.

*Keeping quality*.—Excellent, commonly maintains firmness and juiciness under customary cold storage up to approximately six months.

*Stem locules*.—Commonly approximately 2 cm in length on average, and approximately 9 mm in depth on average.

*Ocular locules*.—Commonly approximately 1.5 cm in length on average, and approximately 1 cm in depth on average.

*Seed number*.—Commonly 7 to 10 on average.

*Seed locules*.—Commonly closed, 5 in number, and typically 1 or 2 seeds are present per locule.

*Seed size*.—Commonly approximately 9 mm in length and approximately 5 mm in width.

*Seed color*.—Commonly near Brown Group 200D.

*Productivity*.—Very good, with appropriate thinning in excess of 20 kg of fruit has been produced in a given season on a seven-year-old tree at Malicorne, France.

Resistance to disease: Resistance to apple scab comparable to that provided by the Vf gene has been observed during observations to date. One of the two parental plants possessed the Vf gene, and after the new cultivar was inoculated with apple scab, resistance has been observed. A slight susceptibility to mildew has been encountered. During observations to date, medium sensitivity to powdery mildew and bitter pit during storage have been encountered.

Hardiness: Well tolerates winter temperatures at Malicorne, France.

Fruit usage: Quality dessert apple with crisp firm flesh, juiciness, and pleasant sweet taste and aroma.

I claim:

1. A new and distinct cultivar of apple tree having the following characteristics:

(a) displays a medium-to-large semi-upright to spreading growth habit, (b) forms attractive large fruit that commonly is ready for harvest later in the season, (c) forms in good yield generally large bright red-purple fruit having an excellent keeping quality wherein the skin coloration is influenced by the degree of exposure to sunlight, and (d) displays very firm fruit flesh having a pleasant juicy sweet taste and flavor upon maturity;

substantially as herein shown and described.

* * * * *